Sept. 19, 1944. D. BONNER Plant Pat. 642
APPLE TREE
Filed Feb. 3, 1944
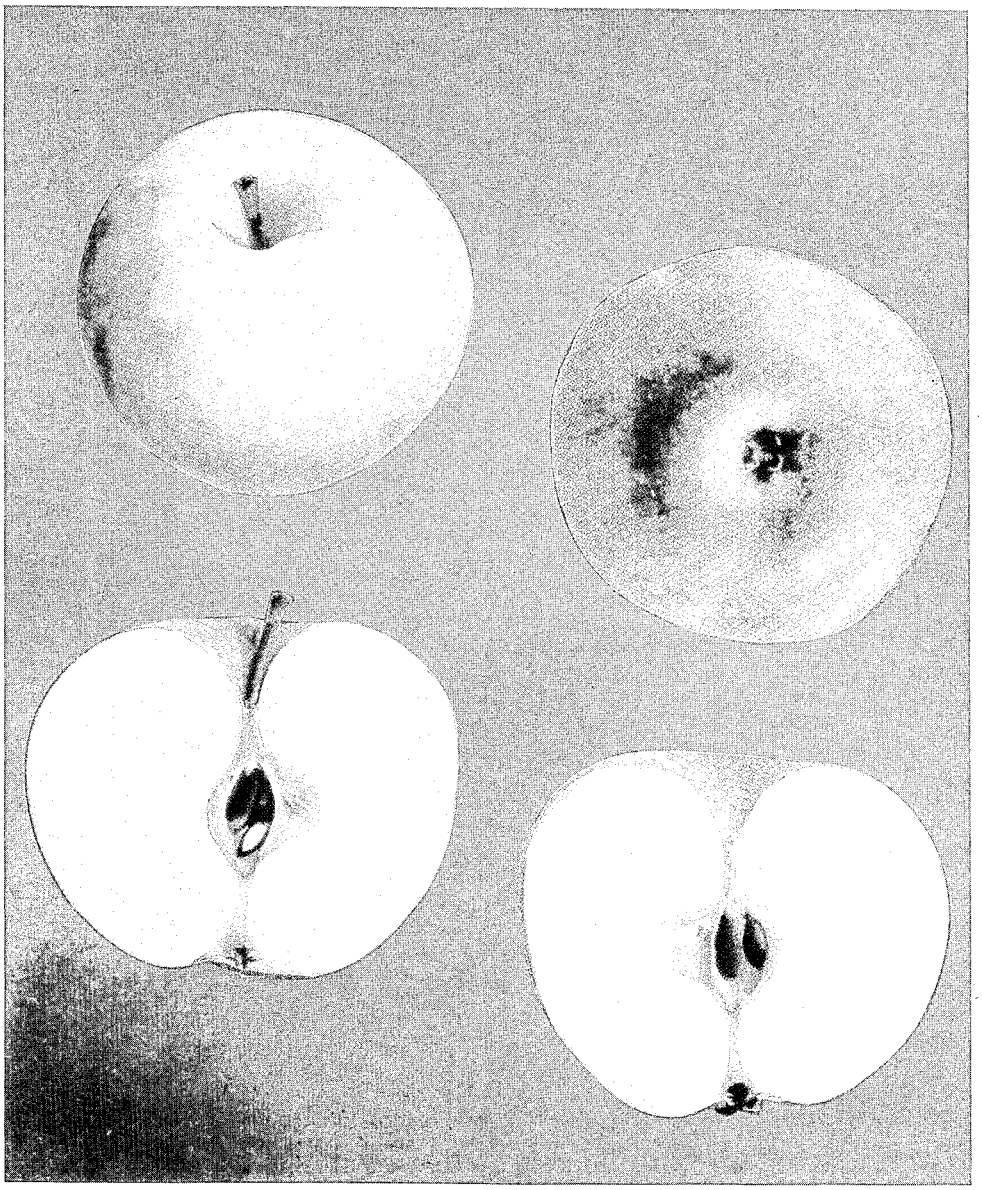
Inventor
Douglas Bonner
By Robb & Robb
Attorneys Patented Sept. 19, 1944

Plant Pat. 642

UNITED STATES PATENT OFFICE

642

APPLE TREE

Douglas Bonner, Orofino, Idaho, assignor to Stark Bro's Nurseries and Orchards Company, Louisiana, Mo.

Application February 3, 1944, Serial No. 520,945

1 Claim. (Cl. 47—62)

The present discovery relates to a new and distinct variety of apple tree, a seedling discovered by me upon my farm in Clearwater County, Idaho.

This new variety has been carefully observed by me, tested and developed over a period of time to determine its permanent characteristics and desirability for commercial purposes.

The results of these observations, including those of its asexual reproductions, are specifically set out hereinafter, but its predominating characteristics which give rise to its value as an all-purpose fruit producer are:

(1) The bright cherry-red blushed fruit.
(2) Good crisp eating quality of the fruit.
(3) Early ripening (by as much as four to seven days) and over a much shorter period than the known varieties "Yellow Transparent" and "Close."
(4) Size intermediate the two varieties mentioned.

As above premised, this new variety, fruit of which is depicted in the accompanying illustration, has been asexually reproduced and the characteristics have been determined to be established.

The following is a detail description of the new variety, color terminology, except where otherwise indicated, being in accord with the usual dictionary significance: (The following observations are made with reference to specimens of the plant grown in Louisiana, Missouri.)

Dates first and last picking—June 26 and July 12, 1943.

Tree:
- Large; vigorous; spreading; dense; round-topped; very rapid growing; hardy; regular bearing.

Trunk:
- Stocky; smooth; greyish in color.

Branches:
- Medium shaggy; branching little; grey-green.
- Lenticels.—Medium number; medium size.

Leaves:
- Average length, 3⅛ inches; width, 1⅞ inches; medium size; medium width; medium length; ovate; apex acute; taper-pointed; medium thick; dark green; rugose.
- *Margin.*—Coarsely serrate.
- *Petiole.*—Length, ¾″–1″; medium length; medium thick.

Fruit:
- Maturity when described—eating hard, June 27, 1943.
- *Size.*—Uniform. Axial diameter—2 inches. Transverse—2¼ inches.
- *Form.*—Oblate.
- *Cavity.* — Symmetrical; even. Depth — ½ inch. Breadth—1 inch. Markings—russet.
- *Basin.* — Unsymmetrical; undulate; fairly pubescent. Depth—$\frac{7}{16}$ inch. Breadth—⅞ inch.

Stem: Clubbed; medium stout; pubescent.
- *Length.*—½ inch.
- *Breadth.*—$\frac{1}{16}$ inch.
- *Markings.*—None.

Calyx: Open; segments persistent; broadly lanceolate; erect; converged from base toward center.
- *Outer surface.*—Pubescent.
- *Inner surface.*—Glabrous.

Eye: Medium size; open.

Skin:
- Thin; tough; smooth; glossy; waxed.
- *Dots.*—Conspicuous; many; large; even; angular.
- *Color of dots.*—Russet.
- *Distribution of dots.*—More numerous at apex.
- *Ground color.*—Citron Yellow (Ridgway's Color Standard).
- *Color markings.*—Striped; splashed; bright.
- *Color of markings.*—Nopal Red (Ridgway's Color Standard).
- *Bloom.*—Scant.
- *General color effect.*—Bright flashy cherry-red blush on attractive yellow.

Flesh: Juicy; yellowish-greenish tint.
- *Texture.*—Firm; tender; granular; crisp.
- *Flavor.*—Subacid; sprightly.
- *Aroma.*—Distinct.
- *Quality*—Good.

Core:
- Median.
- *Bundle area.*—Medium size; oblate; symmetrical; acute at base.
- *Halves of area.*—Equal.
- *Bundles.* — Green-yellowish; inconspicuous, in one whorl.
- *Core lines.*—Clasping, in cross section, indistinct.
- *Carpellary area.*—Distinct.
- *Calyx tube.*—Pubescent; obconic; funnel form.

*Depth of tube to shoulder.*—⅛ inch. Entire depth—¼ inch.
*Styles.*—Present; united; pubescent.
*Stamens.*—In two obscure whorls; median.
*Seed cells.*—Axile; open.
*Cell walls.*—Thin; tough. Length ⅝ inch. Breadth—⅜ inch.
*Longitudinal section.*—Obcordate; mucronate; obtuse at apex.
*Surface.*—Fissured.
*Cross section.*—Broad.

Seeds:
*Number perfect.*—6–7; imperfect, none.
*Number in one cell.*—1–2; length, $\frac{9}{32}$ inch; breadth, $\frac{3}{16}$ inch.
*Form.*—Obtuse.
*Color.* — Liver Brown (Ridgway's Color Standard).

Use:
Market; local; dessert; culinary.

Keeping quality: Medium.
*Number of days in ordinary storage.*—7–10 days.

Resistance to:
Insects—medium.
Diseases—medium.

I claim:

A new and distinct variety of apple tree, characterized as to novelty by the early and short ripening period of its fruit, good crisp eating quality, bright cherry-red blushed color, and medium size of its fruit, substantially as shown and described.

DOUGLAS BONNER.